United States Patent [19]

Schulman et al.

[11] Patent Number: 4,850,972
[45] Date of Patent: Jul. 25, 1989

[54] PROGAMMABLE MULTIPLE PUMP MEDICATION INFUSION SYSTEM WITH PRINTER

[75] Inventors: Joseph H. Schulman, Granada Hills; Lanny A. Gorton, Sunland, both of Calif.

[73] Assignee: Pacesetter Infusion, Ltd., Sylmar, Calif.

[21] Appl. No.: 3,892

[22] Filed: Jan. 16, 1987

[51] Int. Cl.[4] ............................................. A61M 5/00
[52] U.S. Cl. ................................. 604/151; 604/110; 604/67; 128/DIG. 12; 417/286; 417/411; 417/426
[58] Field of Search ............... 604/4, 30, 31, 65, 67, 604/80, 81, 110, 111, 123, 151–155, 66, 131; 128/DIG. 12, DIG. 13, DIG. 1; 417/62, 286, 426, 427, 473, 475, 477, 521, 539, 411

[56] References Cited

U.S. PATENT DOCUMENTS

| | | | |
|---|---|---|---|
| 3,252,623 | 5/1966 | Corbin et al. | 222/59 |
| 3,498,228 | 3/1970 | Blumle et al. | 103/25 |
| 3,543,662 | 12/1970 | Erlichman | 95/11 |
| 3,630,417 | 12/1971 | De Haas | 222/333 |
| 3,809,871 | 5/1974 | Howard et al. | 235/151.3 |
| 4,074,295 | 2/1978 | Kee | 354/145 |
| 4,142,524 | 3/1979 | Jassawalla | 604/123 |
| 4,187,057 | 2/1980 | Xanthopoulos | 604/153 |
| 4,225,410 | 9/1980 | Pace | 204/195 R |
| 4,266,545 | 5/1981 | Moss | 604/110 |
| 4,308,866 | 1/1982 | Jelliffe et al. | 128/214 E |
| 4,324,473 | 4/1982 | Coughlan | 354/276 |
| 4,392,849 | 7/1983 | Petre et al. | 604/66 |
| 4,396,385 | 8/1983 | Kelly et al. | 128/DIG. 12 |
| 4,467,810 | 8/1984 | Vollmann | 128/419 PG |
| 4,479,761 | 10/1984 | Bilstad et al. | 128/DIG. 12 |
| 4,525,163 | 6/1985 | Slavik et al. | 128/DIG. 12 |
| 4,557,725 | 12/1985 | Heyne et al. | 604/151 |
| 4,563,175 | 1/1986 | LaFond | 128/DIG. 12 |
| 4,624,661 | 11/1986 | Arimond | 604/151 |
| 4,631,050 | 12/1986 | Reed et al. | 604/4 |
| 4,634,430 | 1/1987 | Polaschegg | 604/4 |
| 4,712,590 | 12/1987 | Gianfilippo | 604/81 |
| 4,756,706 | 7/1988 | Kerns et al. | 604/66 |

FOREIGN PATENT DOCUMENTS

85/00526 2/1985 PCT Int'l Appl. ................. 604/151

Primary Examiner—Stephen C. Pellegrino
Assistant Examiner—Ralph Lewis
Attorney, Agent, or Firm—Leslie S. Miller

[57] ABSTRACT

A multiple channel medication infusion system is disclosed which has a plurality of disposable pump cassettes mounted on a single main pump unit, thereby making the system compact and resulting in an economic system. The system has a printer which may be connected to the main pump unit to provide a printed record of system operation. Several modes are accessible to set up and program the system, to monitor actual system performance, and to test the system or display warnings indicating system malfunctions or that new cassettes should be installed.

35 Claims, 4 Drawing Sheets

| 07/10/86 | | MODE: SET | | | 15:45:30 |
|---|---|---|---|---|---|
| | PUMP1 | PUMP2 | PUMP3 | PUMP4 | PUMP5 |
| STATUS | OK | OK | OFF | OFF | OFF |
| DRUG | GLUC | SAL | - | - | - |
| DOSE CC | 1000 | 500 | - | - | - |
| RATE CC/H | 500 | 250 | - | - | - |

Fig. 6

| 07/10/86 | | MODE: READ | | | 16:15:30 |
|---|---|---|---|---|---|
| | PUMP1 | PUMP2 | PUMP3 | PUMP4 | PUMP5 |
| STATUS | OK | OK | OFF | OFF | OFF |
| DRUG | GLUC | SAL | - | - | - |
| DOSE CC | 1000 | 500 | - | - | - |
| RATE CC/H | 500 | 250 | - | - | - |
| VOL INF | 500 | 125 | - | - | - |
| TIME LEFT | 90 | 90 | - | - | - |

Fig. 7

| 07/10/86 | | MODE: TEST-WARNING | | | 16:50:30 |
|---|---|---|---|---|---|
| | PUMP1 | PUMP2 | PUMP3 | PUMP4 | PUMP5 |
| STATUS | OK | OK | OFF | OFF | OFF |
| BUBBLE | YES | - | - | - | - |
| PRESSURE | YES | YES | - | - | - |
| BATTERY | OK | - | - | - | - |
| FILTERING | YES | - | - | - | - |
| CHANGE PUMP | YES | - | - | - | - |

PROGAMMABLE MULTIPLE PUMP MEDICATION INFUSION SYSTEM WITH PRINTER

BACKGROUND OF THE INVENTION

Field of the Invention

The present invention relates generally to an electromechanical system for continuously infusing medication into a patient, and more particularly to a single system capable of supplying a plurality of different medications which are to be simultaneously infused into a patient, with the system also being capable of providing a printed record detailing the actual performance of the system over a period of time.

In the past there have been two techniques used to deliver drugs which may not be orally ingested to a patient. The first such technique is through an injection, or shot, which delivers a large dosage at relatively infrequent intervals to the patient. This technique is not always satisfactory, particularly when the drug being administered is potentially lethal or has negative side effects when delivered in a large dosage. This problem results in smaller injections being given at more frequent intervals.

Alternatively, the second technique involves administering a continuous flow of medication to the patient through an IV bottle. Medication may also be delivered through an IV system with an injection being made into a complex maze of IV tubes, hoses, and other paraphernalia. As an alternative to these two techniques of administering medication to a patient, the recent addition of medication infusion pumps has come as a welcome improvement.

Infusion pumps are utilized to administer drugs to a patient in small, metered doses at frequent intervals or, alternatively, in the case of some devices, at a low but essentially continuous rate. Infusion pump therapy may be electronically controlled to deliver precise, metered doses at exactly determined intervals, thereby providing a beneficial gradual infusion of medication to the patient. In this manner, the infusion pump is able to mimic the natural process whereby chemical balances are maintained precisely by operating on a continuous time basis.

Such infusion pumps may use as a power source a battery, which may be either contained inside the main housing of the system, or, alternatively, made integrally as a part of a disposable cassette which includes the actual pump used to precisely meter the amount of medication supplied The combination pump/battery cassette is disclosed in U.S. Pat. No. 4,808,167 entitled "Medication Infusion System With Disposable Pump/Battery Cassette," which was filed simultaneously with this application, is assigned to the assignee of this application, and is hereby incorporated herein by reference. Battery-powered pumps generally use the battery as the power source for the electrical or electronic components used to control the infusion system in addition to using the battery to power the motor or other apparatus used to pump the medication being infused.

Since the portion of the pump through which medication is pumped must be sterile, in most applications of infusion equipment some portion of the equipment must be used only once and then disposed of, typically at regular intervals such as once daily. The pump portion of the infusion pump device is generally the disposable portion, typically designed to be a disposable cassette of inexpensive design, which is easily installable onto the main housing of the system.

One of the problems of existing drug infusion systems is the sheer bulk of such systems, particularly in the case where the patient must have several substances infused. Such systems are useful only to infuse a single medication, so several complete systems must be used. It will be recognized that the bulk of such systems will generally substantially impair the mobility of the patient, often forcing an otherwise ambulatory patient to become bedridden.

In addition, most hospitals have shown substantial resistance to purchasing such systems, since a single patient may require several complete systems As a result, the IV has remained the principal method for infusing medications in hospitals. It is therefore apparent that it would be desirable to provide a medication infusion system which would be capable of infusing a plurality of medical fluids, and this is a primary objective of the present invention.

Presently nurses must maintain a record of medication infused into a patient, whether the medication is infused by an IV or by an infusion system. Such manual record keeping is tedious and subject to error, either in recording of in reading after the initial figures are recorded It is apparent that it is desirable to maintain a written record of medication infused, and it is thus an objective of the present invention to provide for automatic generation of such a written record when desired.

It is also desirable to retain a simple design to minimize the cost of construction both of the system and of the disposable cassette, and to accomplish all these objects in a manner which will retain all of the advantages of reliability, durability, and safety of operation. All the advantages of the present invention will result in a superior medication infusion system having a number of advantages making the system a highly desirable alternative to systems presently available.

SUMMARY OF THE INVENTION

The disadvantages and limitations of the background art discussed above are overcome by the present invention. With this invention, a single medication infusion unit may meter and pump a plurality of medications at different rates and in different quantities. For example, in the preferred embodiment as many as five disposable pump cassettes may be installed onto a single compact infusion pump device The electronic controls contained in the main pump unit are capable of independently driving the multiple pumps at different rates and times to conform to a preset schedule for the particular medication each pump cassette is infusing to a patient.

In the preferred embodiment, one of the cassettes includes a disposable battery which drives the entire device. The cassettes include an interlocking mechanism which ensures that when any one of the cassettes are to be changed, the cassette containing the battery must also be changed. The preferred embodiment also may include a mechanism to ensure that the cassettes are not reused.

A display on the main pump unit provides a visual indication of various system criteria, including display formats to set the operational parameters of the pumps, to monitor the actual performance of the pumps, and to provide warnings of specific problems in the operation of the system. The display also may include various buttons to set the operational parameters of the system, as well as an audible alarm.

In accordance with another aspect of the present invention, provision is made for the main pump unit to connect to an external printing device. By so doing a written record of system performance, setup, and problems may be obtained. The system will store such operational information in memory until the time the printer is connected to the main pump unit. If desired, the printing device may also include provision for programming or testing the main pump unit.

The system of the present invention thus presents a highly favorable alternative to the use of multiple systems in parallel to infuse a plurality of medications into a patient. In fact, the system of the present invention represents a considerable cost savings over the alternative of buying several single channel infusion systems. In addition, the system of the present invention is compact and portable, since it is battery powered. This will restore the mobility to patients having several medications being infused simultaneously.

The present invention also retains the simple design of the disposable cassette, and thus compares favorably to known systems in operational cost. The present invention accomplishes all these objects in a manner which will retain the advantages of reliability, durability, and safety of operation. All the advantages of the present invention will result in a superior multiple medication infusion system having a number of advantages making the system a highly desirable alternative to the use of multiple parallel systems.

DESCRIPTION OF THE DRAWINGS

These and other advantages of the present invention are best understood with reference to the drawings, in which.

DETAILED DESCRIPTION OF THE PREFERRED EMBODIMENT

Figure 1:
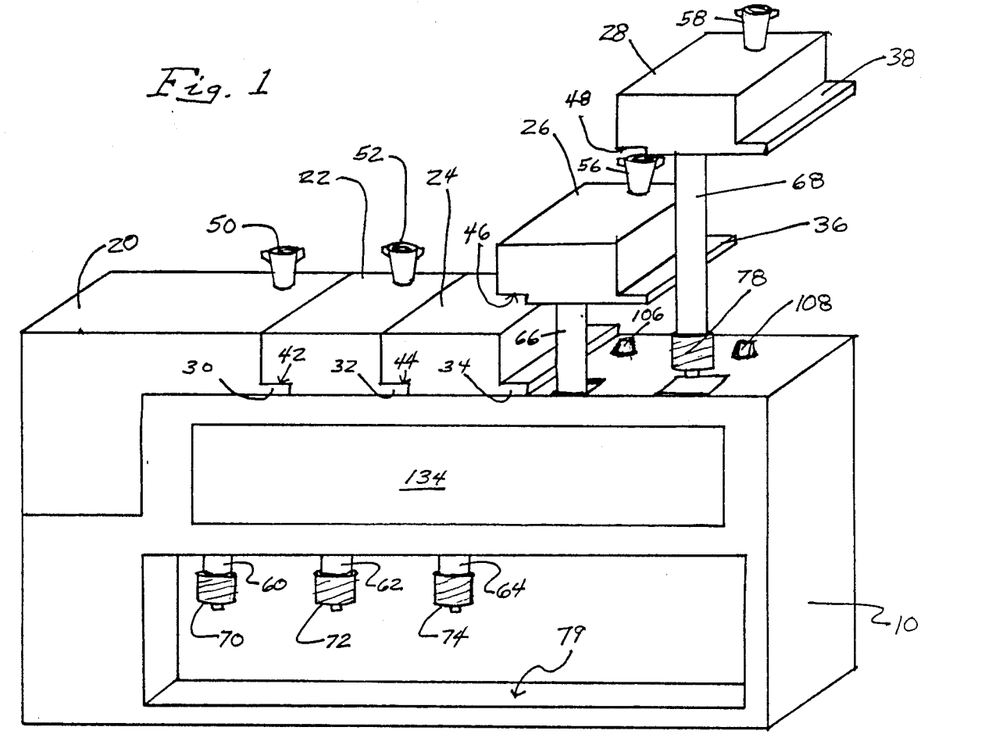
FIG. 1 is a perspective view of a five pump system constructed according to the teachings of the present invention, with one of the cassettes being partially inserted and another being fully withdrawn for detail.

The preferred embodiment of the present invention as embodied in an infusion system having five channels is illustrated in FIG. 1. A main pump unit 10 is illustrated which has an area on the top thereof to which a plurality of disposable cassettes may be attached. In the embodiment illustrated, five cassettes are used, but it will be understood that fewer (or more) may be installed onto a single unit.

A main cassette 20 is installed at one end of the top portion of the main pump unit 10. The main cassette 20 includes therein a battery (not shown) to power the system in addition to a disposable pump. When the main cassette 20 is attached to the main pump unit 10, the battery within is connected to furnish electrical power to the main pump unit 10. Four auxiliary cassettes 22, 24, 26, and 28, each of which contains a disposable pump but no battery, are mounted in sequence across the top portion of the main pump unit 10. The auxiliary cassettes 22, 24, 26, and 28 are all identical, with the main pump unit 10 being capable of accepting up to four of the identical auxiliary cassettes as well as one main cassette containing a battery. It should be noted that the present invention is not limited to the use of a single main cassette 20, but may be arranged and configured to have only cassettes not containing a battery mounted on the main pump unit 10, in which case the power would be supplied from a battery (not shown) contained within the main pump unit 10, or from an external power source (not shown).

Similarly, it would also be within the scope of the present invention to have more than one cassette containing a battery and mounted onto the main pump unit 10. Such a situation would arise particularly in the case when the system is to pump large quantities from more than one pump, or when the system must operate over an extended period of time without changing the cassette(s) containing the battery.

A necessity when the system is operated by a battery in the main cassettes is the periodic replacement of the main cassette 20 well before the battery is exhausted. It has been determined that the frequency with which the main cassette 20 will be replaced is directly dependent on the life of the battery. However, it is also desirable that the auxiliary cassettes 22, 24, 26, and 28 also be replaced periodically, and practicality dictates that the auxiliary cassettes 22, 24, 26, and 28 be replaced at the same time the main cassette 20 is replaced.

In order to ensure that the auxiliary cassettes 22, 24, 26, and 28 are replaced together with the main cassette 20, an interlock system is used by the present invention. The main cassette 20 has a protruding lip 30 which extends from the bottom of the said of the main cassette 20 facing the auxiliary cassette 22, and fits into a matching notch 42 on the lower edge of the auxiliary cassette 22. The notch 42 is on the left side of the auxiliary cassette 22 as mounted on the main pump unit 10 as shown in FIG. 1.

The auxiliary cassette 22 also as a protruding lip 32 on the side opposite the notch 42, on the right side of the auxiliary cassette 22 as depicted in FIG. 1. Likewise, auxiliary cassettes 24, 26, and 28 have protruding lips 34, 36, and 38, respectively, on one side as on the auxiliary cassette 22. The auxiliary cassettes 24, 26, and 28 also have notches 44, 46, and 48, respectively, on the opposite sides from the notches 34, 36, and 38, like the auxiliary cassette 22.

The notches and protruding lips are so arranged and configured to require that the main cassette 20 be installed first, with up to four auxiliary cassettes 22, 24, 26, and 28 being installed sequentially after the installation of the main cassette 20. This safeguard causes the auxiliary cassettes 22, 24, 26, and 28 to be removed before the main cassette 20 can be removed. Since the main cassette 20 contains a battery to power the system and must therefore be periodically replaced, the auxiliary cassettes 22, 24, 26, and 28 must also be periodically replaced in order to replace the main cassette 20.

The system would also have an internal electronic safeguard in the programming to prevent operation auxiliary cassette 24 installed in the location shown in FIG. 1 if the auxiliary cassette 22 were not installed. Small spring loaded switches (not shown) may be mounted in the top of the main pump unit 10 to indicate the presence of cassettes installed on the main pump unit 10. If an auxiliary cassette is installed out of order, i.e. there is an empty slot between the auxiliary cassette in question and the main cassette 20, the auxiliary cassette would be disabled. Failure to have such a safeguard inherent in the system would, of course, defeat the safeguard preventing reuse of auxiliary cassettes when a new main cassette 20 is installed.

Each of the cassettes has an inlet connector thereon, through which a therapeutic fluid from a fluid source (not shown) may be supplied to the cassette. The main cassette 20 has an inlet connector 50, and the auxiliary cassettes 22, 24, 26, and 28 have inlet connectors 52, 54 (not shown), 56, and 58, respectively, mounted thereon. The inlet connectors 50, 52, 54, 56, and 58 are preferably luer connectors, but could be other types of connectors, hose, or other medication supply apparatus.

Each cassette also has outlet apparatus attached thereto, through each of which a therapeutic fluid is pumped in precisely metered quantities, with the fluid being directed eventually to a patient (not shown). An outlet tube 60 having an outlet connector 70 at the outlet end thereof being attached to the main cassette 20. Similarly, outlet tubes 62, 64, 66, and 68, having outlet connectors 72, 74, 76 (not shown), and 78, respectively, at the outlet ends thereof are attached to auxiliary cassettes 22, 24, 26, and 28, respectively. The outlet connectors are also preferably luer connectors, but may be any other suitable connectors.

When the main cassette 20 and the auxiliary cassettes 22, 24, 26, and 28 are installed onto the main pump unit 10, the outlet tubes 60, 62, 64, 66, and 68 extend through apertures in the top of the main pump unit 10. When the main cassette 20 and the auxiliary cassettes 22, 24, 26, and 28 are attached, the outlet connectors 70, 72, 74, 76, and 78 are accessible through a recess 79 in the front of the main pump unit 10. Catheters (not shown) may then be conveniently connected to the outlet connectors 70, 72, 74, 76, and 78.

The main pump unit 10 contains five prime movers for driving the pumps contained in the main cassette 20 and the auxiliary cassettes 22, 24, 26, and 28. In most applications, these prime movers are motors, as shown schematically in FIG. 3. Five motors 80, 82, 84, 86, and 88 in the main pump unit 10 drive five pumps 90, 92, 94, 96, and 98, respectively, which are contained in the main cassette 20 and the auxiliary cassettes 22, 24, 26, and 28, respectively.

The motors 80, 82, 84, 86, and 88 drive the pumps 90, 92, 94, 96, and 98 through mechanical drive connectors 100, 102, 104, 106, and 108, respectively, which extend from the top of the main pump unit 10 and fit in a driving fashion into the main cassette 20 and the auxiliary cassettes 22, 24, 26, and 28. Two of the drive connectors 106, 108 are shown in FIG. 1.

Of course, instead of the motors 80, 82, 84, 86, and 88 a number of other drive mechanisms could be used, such as, for example, a stepper motor, a solenoid apparatus, or a hydraulic motor providing a variable pressure or vacuum. Also, a single motor with a gearing/clutching system could be used to drive all of the multiple pump in the system. The pumps 90, 92, 94, 96, and 98 will be adapted to be driven by the particular prime movers selected, as those skilled in the art will appreciate. The specific types of prime movers and pumps used in not particularly pertinent to the present invention, inasmuch as the present invention works equally well with any drive/pump scheme.

Since the main cassette 20 must be periodically replaced, and since the auxiliary cassettes 22, 24, 26, and 28 must be removed in order to remove the main cassette 20, it may be desirable to utilize a mechanism which will prevent reuse of the cassettes. In a hospital when trained professionals are maintaining the system, the need for such a mechanism may be minimal, but for home use of the system such a mechanism is highly desirable. This mechanism may be accomplished in a variety of ways, with the preferred embodiment being illustrated in FIG. 2. One of the auxiliary cassettes 22 is schematically shown in outline form with the main pump unit 10 being cut away to show the details of the mechanism guarding against reuse.

Figure 2:
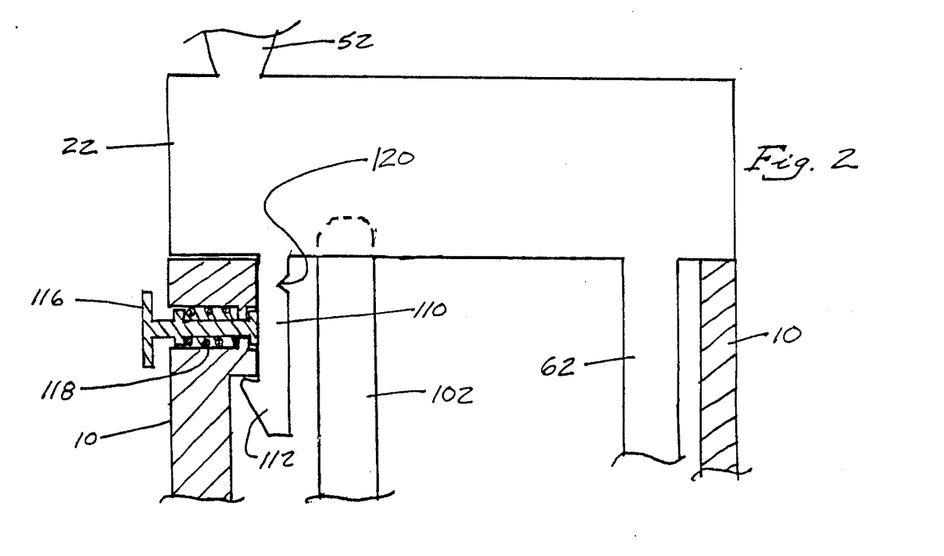
FIG. 2 illustrates a cassette release mechanism located on the back of the device shown in FIG. 1, which will prevent reuse of a cassette, with the main pump housing being cut away for clarity.

The auxiliary cassette 22 has a latch 110 extending from the bottom side thereof, which latch 110 has a hooked end 112. When the cassette 22 is attached to the main pump unit 10, the hooked end 112 snaps onto a sill 114 located inside the back side of the main pump unit 10. The latch 110 will thus secure the cassette 22 to the main pump unit 10.

A release button 116 is mounted on the back side of the main pump unit 10, and extends through the back side to be in contact with the latch 110 when the cassette 22 is attached to the main pump unit 10. The release button 116 is biased by a spring 118 in a direction away from the latch 110. When the release button 116 is pressed, the latch 110 will be pushed inwardly, causing the hooked end 112 to move off of the sill 114, releasing the cassette 22.

There is a breakaway groove 120 in the latch 110, which breakaway groove 120 will be fractured when the release button is pressed. Once the breakaway groove 120 has been fractured, the latch 110 will no longer be able to secure the cassette 22 to the main pump unit 10. This ensures that the cassette 22 will be used only once, and that it will be incapable of being reattached. The other auxiliary cassettes 24, 26, and 28 are constructed similarly to the cassette 22, and in the preferred embodiment the main cassette is also constructed with a latching mechanism like the latch 110. Additional release buttons are located on the back of the main pump unit 10 for all the cassettes.

Figure 3:
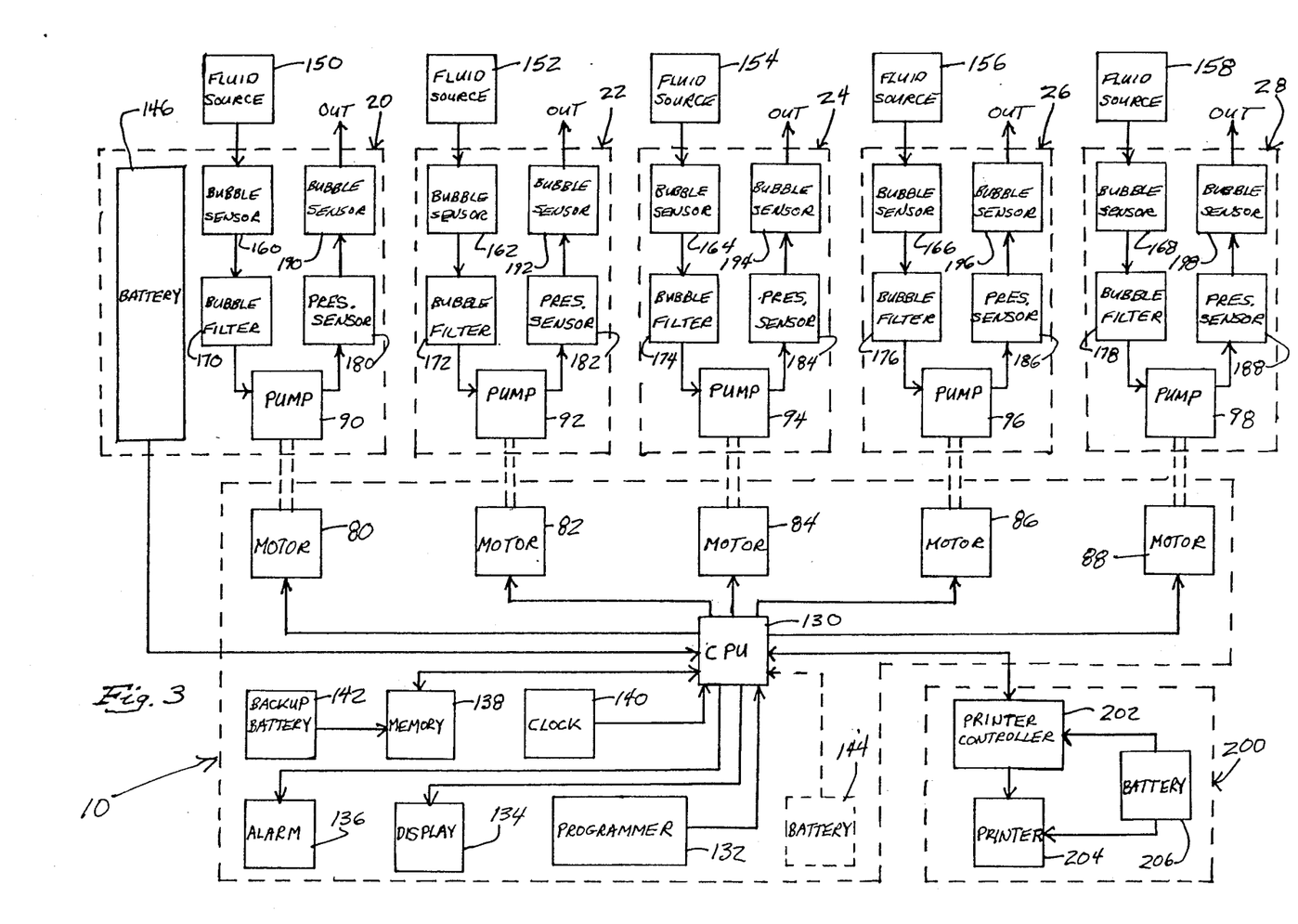
FIG. 3 is a schematic diagram of the infusion system illustrated in FIG. 1, also including a schematic depiction of the disposable cassettes.

The main pump unit 10 has several components illustrated schematically in FIG. 3, with a central processing unit (CPU) 130 representing the heart of the electronic control system. The CPU 130 will control the application of power to the motors 80, 82, 84, 86, and 88 to cause the pumps 90, 92, 94, 96, and 98, respectively, to operate at specific selected rates and at specific selected times.

A programmer 132 is used to set or enter the various parameters of operation of the system, which parameters are supplied to the CPU 130. The programmer 132 may be a keyboard or other manual input device, or it may include either alternatively or in addition to the manual input device receiving facilities for obtaining programming information from an external programming unit (not shown). Typical information entered through the programmer 132 may include various times for various operations to take place, the rate of operations (which would set pump rate), and the lengths of such operations.

A display 134 (also shown as mounted on the main pump unit 10 in FIG. 1) may be provided to provide a visual indication of information entered through the programmer 132, which display 134 receives output signals from the CPU 130. The display 134 may also be used to provide information of the operation of the system during operation of the system, in which case the display 134 would be of a low power type, such as an LCD display. Such information would be of a transitory nature, and would generally include only a summary of historical operation of the system, and not informational parameters varying over time.

An audible alarm 136 is used to indicate successful entry of information, errors in entering the information, etc. The CPU 130 is able to store and access information from a memory 138, and is supplied with signals from a clock 140.

A backup battery 142, typically a long life lithium or similar battery, is used to sustain the memory 138 and the CPU 130 during times when a new main cassette 20 is being installed and no main power source is present. Alternately, a low-leakage, high value capacitor (not shown) may be used instead of the backup battery 142, with such a capacitor being capable of powering the memory 138 for at least a week or so. In this case, the battery in the main cassette 20 would be used to recharge the low-leakage high value capacitor. An internal battery 144 is shown in phantom lines, and represents an optional power source for the infusion system which, though not included in the preferred embodiment, may be included to operate a system having high pumping rates or extended times between changes of the main cassette 20. Another possibility contemplated by the present invention, although not included in the preferred embodiment, is the use of more than one cassette with a battery contained integrally therein. The furthest extension of this alternate embodiment would be the inclusion of a battery in each cassette, so that a single battery would be provided to drive each pump.

Referring still to FIG. 3, the construction of the main cassette 20 and the auxiliary cassettes 22, 24, 26, and 28 is schematically illustrated. The auxiliary cassettes 22, 24, 26, and 28 are identical to the main cassette 20 except for the fact that the main cassette 20 includes a battery 146. The main cassette 20 and the auxiliary cassettes 22, 24, 26, and 28 receive therapeutic fluids from fluid sources 150, 152, 154, 156, and 158, respectively, and provide fluid outputs as mentioned previously in conjunction with the discussion of FIG. 1.

Fluid enters the main cassette 20 from the fluid source 150, and enters an inlet bubble sensor 160. The bubble sensor 160 is used to detect the presence of an air bubble passing through the line. Such bubble detectors typically use a light source on one side of the line and a light sensor on the other side of the line, with the amount of light passing through the line changing when a bubble is present. In addition to this transmission based sensor other types of bubble detectors include reflection, impedance, radio wave, sound wave, magnetic, and nuclear bubble detectors, which are known in the art. Information from the inlet bubble sensor 160 is provided to the CPU 130, which monitors performance in addition to operating the infusion system. At this time, in the preferred embodiment, an alarm will be provided to indicate the presence of a bubble.

When a bubble is detected in the fluid line following the inlet bubble sensor 160, a bubble filter 170 will remove the bubble. The bubble will thusly be removed before reaching the pump 90, which enables the system to maintain a high degree of accuracy. If the bubble is not removed from the line before entering the pump 90, pumping accuracy would be adversely affected. In addition, the pump 90 may in some instances be blocked by an air bubble.

Following the pump 90 is a pressure sensor 180, which will provide information to the CPU 130 as to the output pressure of the pump 90. Pressure sensing is important both for detecting loss of pressure indicating a system malfunction and for detecting excessively high pressure indicating an occlusion or blockage in the output line. The pressure sensor 180 may be any of a number of known designs producing an electrical output, and like all of the devices in the disposable cassettes is preferably of an economical design.

In the preferred embodiment, an outlet bubble sensor 190 is also incorporated in the cassette 20, and provides a signal to the CPU 130. The outlet bubble sensor 190 is the last device in the flow path within the cassette 20, and if it detects the presence of a bubble in the line the pump 90 will be shut down immediately and an alarm will be sounded.

The auxiliary cassettes 22, 24, 26, and 28 have similar components therein, including inlet bubble sensors 162, 164, 166, and 168, respectively, bubble filters 172, 174, 176, and 178, respectively, pressure sensors 182, 184, 186, and 188, respectively, and outlet bubble sensors 192, 194, 196, and 198, respectively. These components operate in a similar manner to the components in the main cassette 20, and each cassette is operated independently. A failure in one pump will therefore not necessarily shut down the other pumps.

The main pump unit 10 has a connector for communication with a printer system 200. The printer system 200 may be periodically connected to the main pump unit 10 to access historical or operational information on pump operation which is stored in the memory 138. The printer system 200 may be miniature, like those used in small printing calculators, and may even, if desired, be made integrally with the main pump unit 10. The printer system 200 includes a printer controller 202 and a printer 204. The printer controller selects the operation desired for printing, and controls the printer 204. A battery 206 may also be included to power the printer system 200, or AC power may be used to operate it.

Figure 4:
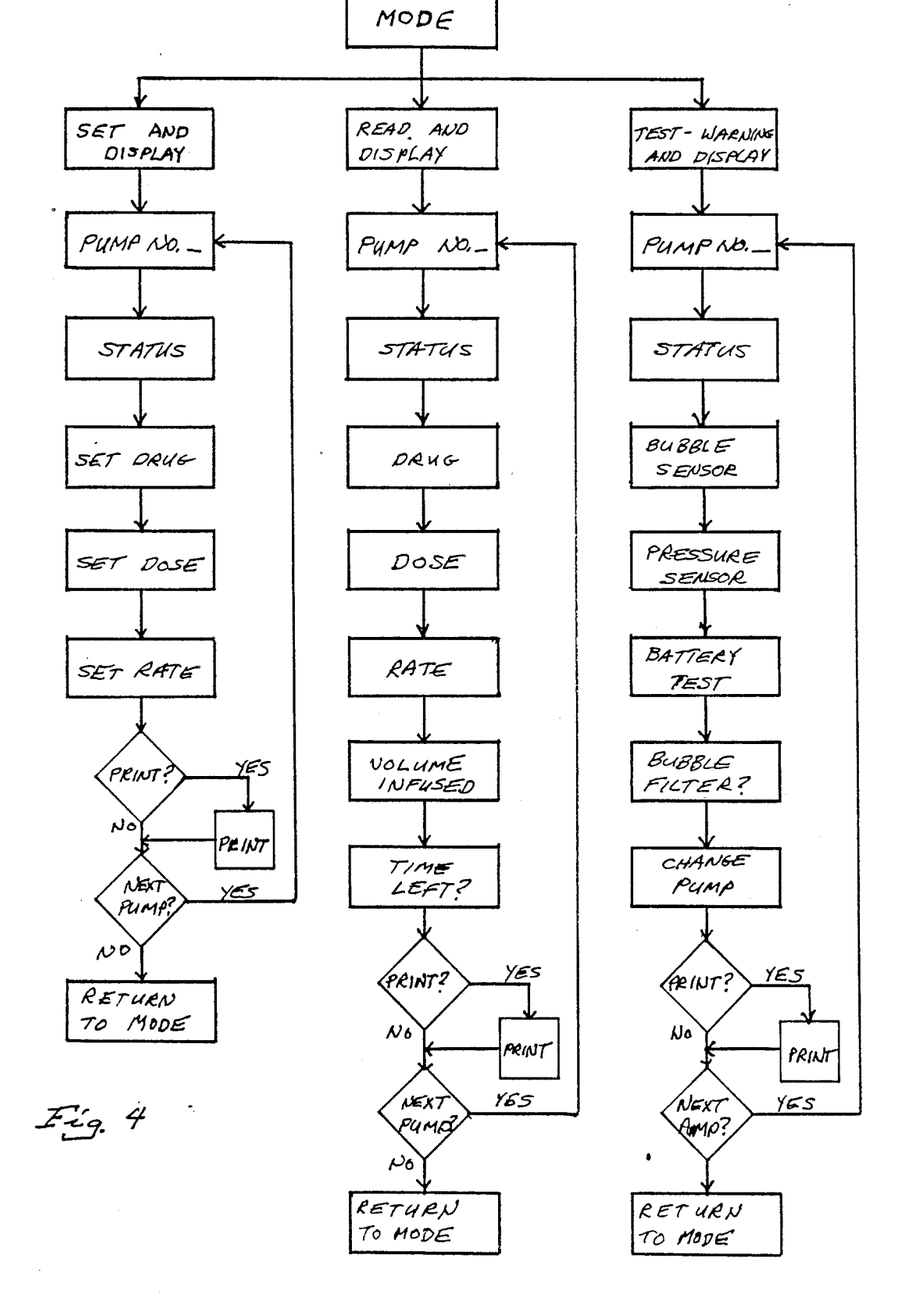
FIG. 4 is a flowchart of the three operational modes of the system shown in the previous Figures, including a set mode, a display operational history mode, and a test or warning mode.

FIG. 4 illustrates the modes of operation used by the system of the preferred embodiment to set and obtain the information to be displayed (and printed, if the printer system 200 is connected). One of three modes is selected, the three modes being set and display, which is used to program the system for operation. The pumps are programmed in order, with the main cassette 20 being defined as pump 1, the auxiliary cassette 22 being pump 2, the auxiliary cassette 24 being pump 3, the auxiliary cassette 26 being pump 4, and the auxiliary cassette 28 being pump 5.

Figure 5:
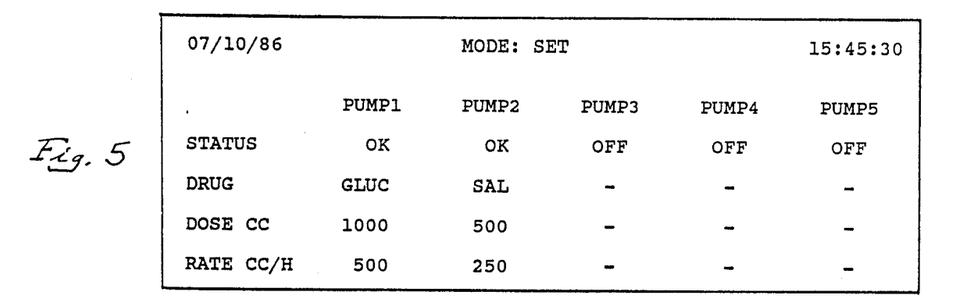
FIG. 5 is an example of a printout obtained in the "set" mode.

The status of the pump is set first, and status is either on or off. Referring to FIG. 5 in addition to FIG. 4, an example of the printout for the set and display mode is illustrated. When the pump is turned on, the printout will indicate OK (assuming no system malfunctions). The type of drug being infused is provided to the system, as is the dose and the rate of infusion desired. The rate, for example, is provided in cc's per hour, and the dose is the total amount to be infused. This information is printed, together with the date and time, as shown in FIG. 5. A record is thereby obtained of the prescribed medication infusion regimen to be followed.

Figure 6:
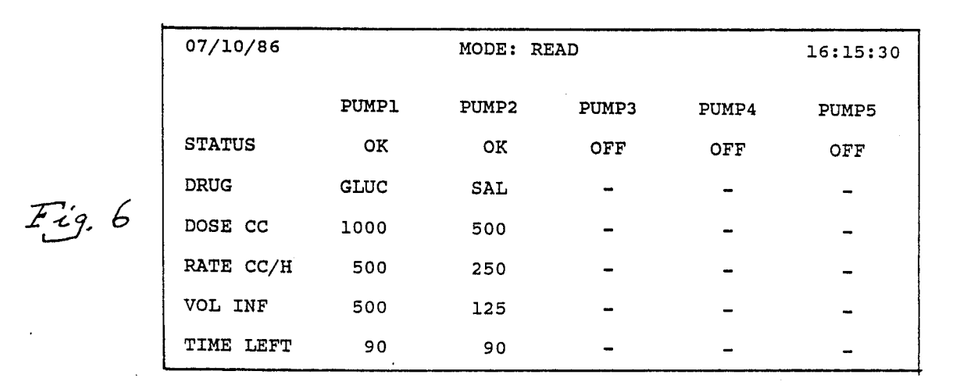
FIG. 6 is an example of a printout obtained in the "display" mode.

The second mode of operation is a read and display mode, which may be accessed to provide information on system performance. The information on pump performance is accessed from the memory 138 and provided as a visual output on the display 134 and through the printer system 200, if desired. The drug being infused, the dose, the rate, the actual volume of the drug infused at that point in time, and the time left before the dose is administered are indicated. Information for each succeeding pump is provided, in a printout as shown in FIG. 6, or for one pump at a time on the display 134.

A third mode is a test-warning and display mode, in which status of each pump is indicated. The test-warning mode is shown in FIG. 4, with an example of a printout in this mode being shown in FIG. 7. Whether on not the inlet bubble sensor indicated the presence of a bubble is indicated, and whether the bubble filter is operating (or has operated) is also indicated. Whether or not the pressure sensor output is in the proper range is indicted, and if the cassette contains a battery the battery level is also indicated. Finally, if there has been a malfunction, or if it is time to install a new cassette, an indication to change the pump will be given.

Figure 7:
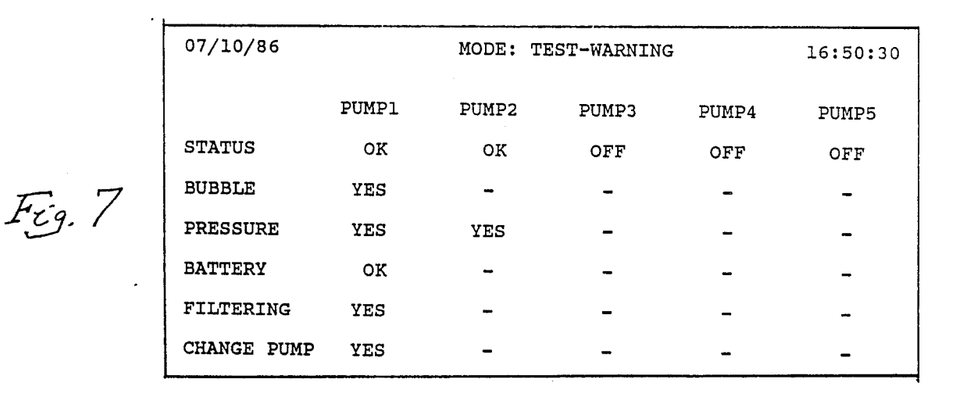
FIG. 7 is an example of a printout obtained in the "testwarning" mode.

In the example of pump 1 shown in FIG. 7, pumps 1 and 2 are operating correctly, an OK are provided for both. If not, a signal indicating a malfunction or an error would be provided. The inlet bubble sensor for pump 1 is sensing (or has sensed) a bubble, while the inlet bubble sensor for pump 2 has not. The pressure sensors for both pump 1 and pump 2 are within proper limits. The battery for pump 1 (which is the main cassette 20) is OK, and the bubble filter for pump 1 is operating or has operated. Finally, the change pump signal for pump 1 only is indicated, meaning that there has been a failure. Had it been time to replace the pumps, the change pump signal would have been indicated for both pumps 1 and 2 (unless pump 2 was installed at a later time than pump 1).

It is therefore apparent that the system of the present invention presents a highly favorable alternative to the use of multiple systems in parallel to infuse a plurality of medications into a patient. The system of the present invention is compact, portable, and battery powered, making it and a patient using it highly mobile. It also represents a considerable cost savings over the alternative of buying several single channel infusion systems, and retains the simple (and inexpensive) design of the disposable cassette. The present invention is also highly dependable and safe in operation, and presents a convenient printed record of operation, thusly making it a highly desirable medical infusion system.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A medication infusion system for infusing a plurality of fluids into a living body, comprising:
    a main cassette including therein a first fluid pump having an inlet to which a first fluid is supplied from a first source, and an outlet from which said first fluid is pumped, said main cassette also including therein a battery for providing power to said system;
    at least one auxiliary cassette including therein a second fluid pump having an inlet to which a second fluid is supplied from a second source, and an outlet from which said second fluid is pumped;
    a main pump unit onto which said main cassette and said auxiliary cassette may be removably attached;
    a first prime mover comprising the means for driving said first fluid pump, said first prime mover being mounted in said main pump unit;
    a second prime mover comprising the means for driving said second fluid pump, said second prime mover being mounted in said main pump unit;
    electronic controller means for controlling the operation of said first and second prime movers, said electronic controller means controlling each of said first and second prime movers independently to cause said first and second prime movers to drive said first and second pumps independently of each other, said electronic controller means being mounted in said main pump unit; and
    electrical connecting means for electrically connecting said battery to said electronic controller means, said electrical connecting means comprising a first connecting means mounted in said main cassette and a second connecting means mounted in said main pump unit.

2. A medication infusion system as defined in claim 1, additionally comprising:
    an inlet connector on said main cassette through which said first therapeutic fluid is supplied to said main cassette;
    an outlet connector on said main cassette through which said first therapeutic fluid is pumped by said main cassette;
    an inlet connector on said auxiliary cassette through which said second therapeutic fluid is supplied to said auxiliary cassette; and
    an outlet connector on said auxiliary cassette through which said second therapeutic fluid is pumped by said auxiliary cassette.

3. A medication infusion system as defined in claim 2, wherein said inlet connectors and said outlet connectors are luer connectors.

4. A medication infusion system as defined in claim 1, additionally comprising:
    means on said main pump unit for altering said main cassette and said auxiliary cassette to prevent their reuse after initial detachment from said main pump unit.

5. A medication infusion system as defined in claim 4, wherein said altering means comprises:
    a latch mounted on at least one of said main cassette and said auxiliary cassette;
    a sill on said main pump unit for receiving said latch when said one of said main cassette and said auxiliary cassette is attached to said main pump unit, said latch retaining said one of said main cassette and said auxiliary cassette in position on said main pump unit
    a breakaway groove on said latch; and
    means for breaking said breakaway groove on said latch to release said one of said main cassette and said auxiliary cassette from said main pump unit, said one of said main cassette and said auxiliary cassette thereafter being unattachable to said main pump unit, said breaking means being mounted on said main pump unit.

6. A medication infusion system as defined in claim 5, wherein said breaking means comprises:
   a releaser button mounted on said pump unit, said release button contacting said latch when pushed to break or bend said latch at said breakaway groove; and
   a spring to preload said button in a position away from said latch.

7. A medication infusion system as defined in claim 4, additionally comprising:
   interlock means located on said main cassette and said auxiliary cassette for preventing the removal of said main cassette until any and all auxiliary cassettes have been first removed.

8. A medication infusion system as defined in claim 7, wherein said interlock means comprises:
   a protruding lip extending from one side of said main cassette facing said auxiliary cassette and at a location near said main pump unit; and
   a notch in said auxiliary cassette on the side facing said main cassette and at a location near said main pump unit, said notch for receiving said protruding lip to thereby prevent the removal of said main cassette without first removing said auxiliary cassette.

9. A medication infusion system as defined in claim 8, additionally comprising:
   a protruding lip extending from one side of said auxiliary cassette on the side opposite said notch and at a location near said main pump unit.

10. A medication infusion system as defined in claim 1, additionally comprising:
    means located in said main cassette and in said auxiliary cassette for sensing one or more parameters of fluid in at least one of said main cassette and said auxiliary cassette.

11. A medication infusion system as defined in claim 10, wherein sensing means comprises:
    a bubble sensor for detecting air bubbles in the fluid line before a pump; and
    a bubble filter for removing air bubbles in the line before the pump.

12. A medication infusion system as defined in claim 10, wherein said sensing means comprises:
    a bubble sensor for detecting air bubbles in the fluid line after a pump; and
    means for shutting down the system upon detection of an air bubble by said bubble sensor.

13. A medication infusion system as defined in claim 10, wherein said sensing means comprises:
    a pressure sensor for detecting either loss of pressure, indicating a system malfunction, or excessively high pressure, indicating an occlusion or blockage in an output line.

14. A medication infusion system as defined in claim 1, additionally comprising:
    means located in said main pump unit for coupling an output of said first prime mover to drive said first fluid pump; and
    means located in said main pump unit for coupling an output of said second prime mover to drive said second fluid pump.

15. A medication infusion system as defined in claim 1, wherein said electronic controller means has as inputs used to control said system the rate at which each of said plurality of therapeutic fluids is to be infused and the total volume of each of said plurality of therapeutic fluids to be infused.

16. A medication infusion system as defined in claim 1, wherein said electronic controller means includes means for calculating informational outputs including the specific volume of each of said plurality of therapeutic fluids infused.

17. A medication infusion system as defined in claim 1, additionally comprising:
    a printer for printing at least a portion of operational information describing the operation of said system, said printer for connection to said electronic controller.

18. A medication infusion system as defined in claim 17, additionally comprising:
    means for sensing one or more parameters of fluid in at least one of said main cassette and said auxiliary cassette, said printer being so arranged and configured as to print sensed information.

19. A medication infusion system as defined in claim 17, additionally comprising:
    electronic means for calculating informational outputs including the specific volume of each of said plurality of therapeutic fluids infused, wherein said printer is so arranged and configured as to print one of said calculated informational outputs.

20. A medication infusion system as defined in claim 17, additionally comprising:
    operational information used to control the rate at which each of said plurality of therapeutic fluids is to be infused and the total volume of each of said plurality of therapeutic fluids to be infused, wherein said printer is so arranged and configured as to print at least a portion of said operational information.

21. A medication infusion system as defined in claim 20, wherein said printer is also arranged and configured to print the associated time correlated with said operational information.

22. A medication infusion system as defined in claim 17, wherein said printer is detached from or detachable from said main pump unit.

23. A medication infusion system as defined in claim 17, wherein said printer is mounted in said main pump unit.

24. A medication infusion system as defined in claim 17, additionally comprising:
    mode selection means for selecting one of a plurality of modes of operation for said system, said modes being used to display and/or print a variety of information.

25. A medication infusion system as defined in claim 24, wherein said system operates in a set and display mode to allow the rate of infusion and total volume to be infused to be set for each of the therapeutic fluids to be infused.

26. A medication infusion system as defined in claim 24, wherein said system operates in a read and display mode which may be accessed to provide information on system performance including the actual volume of each of the therapeutic fluids infused at that point in time.

27. A medication infusion system as defined in claim 24, wherein said system operates in a test/warning and display mode in which malfunctions are indicate and battery level is monitored.

28. A medication infusion system as defined in claim 17, wherein said printer prints operational information describing the operation of each of said fluid pumps.

29. A medication infusion system as defined in claim 1, wherein said electronic controller means comprises:
means for setting, monitoring, and testing each of said fluid pumps.

30. A medication infusion system as defined in claim 1, additionally comprising:
at least one additional auxiliary cassette, including therein an additional fluid pump having an inlet to which an additional fluid is supplied from an additional source, and an outlet from which said additional fluid is pumped; and
at least one additional prime mover comprising the means for driving said additional fluid pump.

31. A medication infusion system for infusing a plurality of fluids into a living body, comprising:
a main pump unit;
a plurality of disposable fluid pumps for removable installation onto said main pump unit, at least one of said disposable fluid pumps having a battery attached thereto and disposable therewith, said battery for providing power to said main pump unit;
a plurality of motors located in said main pump unit, said motors comprising the means for driving said plurality of disposable fluid pumps;
electronic controller means located in said main pump unit for independently controlling the operation of each of said plurality of motors, thereby controlling the rate of fluid flow, the amount of fluid pumped, and the time at which fluid is pumped by each of said disposable fluid pumps; and
electrical connecting means for electrically connecting said battery to said electronic controller means, said electrical connecting means comprising a first connecting means mounted in said one of said disposable fluid pumps having a battery attached thereto and a second connecting means mounted in said main pump unit.

32. A medication infusion system for infusing a plurality of fluids into a living body, comprising:
a first fluid pump having an inlet to which a first fluid is supplied from a first source, and an outlet from which said first fluid is pumped in precisely metered amounts at preselected times;
first cassette housing means for containing said first fluid pump in an integral package defining a first disposable cassette, said inlet and said outlet of said first pump being mounted in said first cassette, said first disposable cassette for removable attachment to a main pump unit, said first disposable cassette being disposable after one use;
a second fluid pump having an inlet to which a second fluid is supplied from a second source, and an outlet from which said second fluid is pumped in precisely metered amounts at preselected times;
second cassette housing means for containing said second fluid pump in an integral package defining a second disposable cassette, said inlet and said outlet of said second pump being mounted in said second cassette, said second disposable cassette for removable attachment to a main pump unit, said second disposable cassette being disposable after one use;
main pump unit housing means for containing a plurality of components;
a first prime mover comprising the means for driving said first fluid pump, said first prime mover being mounted in said main pump unit housing means;
a second prime mover comprising the means for driving said second fluid pump, said second prime mover being mounted in said main pump unit housing means;
electronic controller means for controlling the operation of said first and second prime movers, said electronic controller means controlling each of said first and second prime movers independently to cause said prime movers to cause said first and second fluid pumps to pump said precisely metered amounts at said preselected times, said electronic controller means being mounted in said main pump unit housing means;
a battery for powering at least one of said prime movers or said electronic controller means, or a combination thereof, said battery being contained in and disposable with said first cassette housing; and
electrical connecting means for electrically connecting said battery to said electronic controller means, said electrical connecting means comprising a first connecting means mounted in said first cassette housing and a second connecting means mounted in said main pump unit housing means.

33. A medication infusion system for infusing a plurality of fluids into a living body, comprising:
a first cassette housing;
a first fluid pump having an outlet to which a first fluid is supplied from a first source, and an outlet from which said first fluid is pumped in precisely metered amounts at preselected times, said first fluid pump being mounted in said first cassette housing;
a second cassette housing;
a second fluid pump having an inlet to which a second fluid is supplied from a second source, and an outlet from which said second fluid is pumped in precisely metered amounts at preselected times, said second fluid pump being mounted in said second cassette housing;
a main pump unit housing;
a first prime mover comprising the means for driving said first fluid pump, said first prime mover being mounted in said main pump unit housing;
a second prime mover comprising the means for driving said second fluid pump, said second prime mover being mounted in said main pump unit housing;
electronic controller means for controlling the operation of said first and second prime movers, said electronic controller means controlling each of said first and second prime movers independently to cause said prime movers to cause said first and second fluid pumps to pump said precisely metered amounts at said preselected times, said electronic controller means bring mounted in said main pump unit housing;
a battery for powering at least one of said prime movers or said electronic controller means, or a combination thereof, said battery being attached to and disposable with said first fluid pump, said battery being mounted in said first cassette housing;
electrical connecting means for electrically connecting said battery to said electronic controller means said electrical connecting means comprising a first connecting means mounted in said first cassette housing and a second connecting means mounted in said main pump unit housing; and means for providing a record of information relating to fluid pumped by said first and second fluid pumps, said means for providing a record being operatively connected to said electronic controller means and mounted in said main pump unit housing.

34. A method of infusing a plurality of medical fluids into a living body, comprising:

providing a main pump unit;

installing a plurality of disposable fluid pumps on said main pump unit, at least one of said disposable fluid pumps having a battery attached thereto and disposable therewith, said battery being connected to provide power to said main pump unit;

driving said plurality of disposable fluid pumps with a plurality of motors, said motors being located in said main pump unit; and independently controlling the operation of each of said plurality of motors with an electronic controller, thereby controlling the rate of fluid flow, the amount of fluid pumped, and the time at which the fluid is pumped by each of said disposable fluid pumps.

35. A method of infusing a plurality of medical fluids into a living body, comprising:

providing a disposable main cassette, including therein a fluid pump having an inlet to which said fluid is supplied from a source, and an outlet from which said fluid is pumped in precisely metered amounts at preselected times;

providing a disposable auxiliary cassette including therein a disposable fluid pump having an inlet to which said fluid is supplied from a source, and an outlet from which said fluid is pumped in precisely metered amounts at preselected times;

driving said disposable fluid pump in said main cassette with a first prime mover;

driving said disposable fluid pump in said auxiliary cassette with a second prime mover;

controlling the operation of said first and second prime movers with an electronic controller to cause said disposable fluid pumps in said main and auxiliary cassettes to pump said precisely metered amounts at said preselected times; and powering at least one of said first prime mover, said second prime mover, and said electronic controller with a battery, said battery being contained in said main cassette, said battery being connected to drive said first prime mover, said second prime mover, and said electronic controller.

* * * * *